(12) United States Patent
Ravikumar

(10) Patent No.: US 6,592,535 B2
(45) Date of Patent: Jul. 15, 2003

(54) METHODS AND APPARATUS FOR ARRESTING SCALP BLEEDING

(76) Inventor: Sundaram Ravikumar, 265 Hardscrabble Rd., Briarcliff Manor, NY (US) 10510

(*) Notice: Subject to any disclaimer, the term of this patent is extended or adjusted under 35 U.S.C. 154(b) by 0 days.

(21) Appl. No.: 09/886,541

(22) Filed: Jun. 20, 2001

(65) Prior Publication Data

US 2002/0198480 A1 Dec. 26, 2002

(51) Int. Cl.[7] ............................................. A61F 5/00
(52) U.S. Cl. ............................ 602/13; 602/17; 602/74
(58) Field of Search ........................... 602/13, 53, 17, 602/74; 2/68, 413, 423, 171, 171.2, 175.4, 425, 209, 200.3

(56) References Cited

U.S. PATENT DOCUMENTS

| | | |
|---|---|---|
| 865,254 A | 9/1907 | Kappmeier |
| 1,567,931 A | 7/1925 | Epler |
| 2,206,481 A | 7/1940 | Luchs et al. ............... 128/399 |
| 2,256,683 A | 9/1941 | Mikesell ..................... 128/163 |
| 2,823,668 A | 2/1958 | Van Court ................... 128/87 |
| 3,050,064 A | 8/1962 | Moore ......................... 128/327 |
| 3,159,160 A | 12/1964 | Ullom ......................... 128/97 |
| 3,171,410 A | 3/1965 | Towle, Jr. ................... 128/155 |
| 3,491,761 A | 1/1970 | Baker ......................... 128/42 |
| 3,659,609 A | 5/1972 | Arouete ...................... 128/325 |
| 3,709,225 A | 1/1973 | Sobel ......................... 128/254 |
| 3,954,109 A | 5/1976 | Patel .......................... 128/327 |
| 4,005,709 A | 2/1977 | Laerdal ....................... 128/155 |
| 4,190,054 A | 2/1980 | Brennan ...................... 128/402 |
| 4,207,885 A | 6/1980 | Hampton ..................... 128/156 |
| 4,210,147 A * | 7/1980 | Nestor et al. ................ 606/202 |
| 4,669,476 A | 6/1987 | Gordon ....................... 128/399 |
| 4,706,673 A | 11/1987 | Meistrell ..................... 128/402 |
| 4,805,620 A | 2/1989 | Meistrell ..................... 128/402 |
| 5,014,365 A * | 5/1991 | Schulz ........................ 2/412 |
| 5,031,246 A * | 7/1991 | Kronenberger ............. 2/195.2 |
| 5,031,609 A | 7/1991 | Fye ............................. 128/163 |
| 5,188,103 A | 2/1993 | Smith ......................... 128/380 |
| 5,349,702 A * | 9/1994 | Runckel ...................... 2/68 |
| 5,628,723 A | 5/1997 | Grau .......................... 602/53 |
| 5,713,188 A | 2/1998 | Chisholm ................... 54/80.1 |
| 5,897,582 A | 4/1999 | Agnatovech ................ 607/109 |
| 6,171,271 B1 | 1/2001 | Hornberg .................... 602/13 |
| 6,183,501 B1 | 2/2001 | Latham ....................... 607/109 |

* cited by examiner

*Primary Examiner*—Nicholas D. Lucchesi
*Assistant Examiner*—Lalita M Hamilton
(74) *Attorney, Agent, or Firm*—David P. Gordon; David S. Jacobson; Thomas A. Gallagher

(57) ABSTRACT

An apparatus for arresting scalp bleeding includes skull cap having a plurality of inflatable bladders and a pump for inflating the bladders. The methods of the invention include attaching the skull cap to the bleeding victim and inflating the bladders with air using the pump. The inflated bladders exert pressure on the bleeding scalp and result in a hemostasis. According to the presently preferred embodiments, the skull cap has three or four independently inflatable bladders and the pump is a hand pump of the type used to inflate a blood pressure cuff. The pump is preferably provided with a pressure gauge and the bladders are each inflated to about 80 mm Hg.

8 Claims, 3 Drawing Sheets

METHODS AND APPARATUS FOR ARRESTING SCALP BLEEDING

BACKGROUND OF THE INVENTION

1. Field of the Invention

The invention relates to a hemostatic device and methods for its use. More particularly, the invention relates to an inflatable hemostasis device for treating a bleeding scalp at the scene of an emergency and to methods for using it.

2. State of the Art

Head injuries are typically traumatic, often associated with automobile accidents and the like. The severity of a head injury is very difficult to diagnose, particularly at the scene of an emergency. Serious head injuries, such as those involving internal bleeding, may present few or no visible symptoms. Conversely, relatively minor scalp wounds will bleed profusely.

Although profusely bleeding scalp wounds may be minor injuries, their presence has a terrifying effect on the victim and others at the scene of an accident. Moreover, the loss of blood resulting from such an injury can complicate other more serious injuries. Emergency medical technicians often waste time dealing with minor head injuries which exhibit profuse bleeding. While this time is being wasted, other more serious injuries may go unattended.

At present, there is no simple, quick, and efficient way to arrest scalp bleeding.

SUMMARY OF THE INVENTION

It is therefore an object of the invention to provide methods and apparatus for arresting scalp bleeding.

It is also an object of the invention to provide methods and apparatus for arresting scalp bleeding at the scene of an emergency.

It is another object of the invention to provide methods and apparatus for arresting scalp bleeding which are easily implemented by emergency medical technicians at the scene of an emergency.

It is still another object of the invention to provide an apparatus for arresting scalp bleeding which is inexpensive and easy to manufacture.

In accord with these objects which will be discussed in detail below, the apparatus of the present invention includes a skull cap having a plurality of inflatable bladders and a pump for inflating the bladders. The methods of the invention include attaching the skull cap to the bleeding victim and inflating the bladders with air using the pump. The inflated bladders exert pressure on the bleeding scalp and result in a hemostasis. According to the presently preferred embodiments, the skull cap has three or four independently inflatable bladders and the pump is a hand pump of the type used to inflate a blood pressure cuff. The pump is preferably provided with a pressure gauge and the bladders are each inflated to a pressure of about 80 mm Hg. According to the presently preferred embodiments, the cap is made from two layers: an inner rubber layer and an outer nylon/non-absorbent fabric layer. The bladders are preferably fluidly coupled to inflation tubes having releasable valves which are located at a single location on the cap for rapid inflation with the pump. The cap is preferably designed to lie flat when not in use, has two ear openings and three lobes, each of which carries a bladder, a fourth bladder arranged to lie in the region of the forehead, and a VELCRO fastening strap. According to the preferred methods of the invention, the cap is placed over the head of the victim such that one lobe lies adjacent to the back of the head and one lobe lies on left and right sides of the head with the victims ears protruding through the ear openings. The VELCRO strap extends from one side of the victim's head across the back to the other side. According to an alternate, less preferred embodiment, the fourth bladder in the region of the forehead may be omitted. According to another embodiment of the invention, the skull cap includes means for attaching it to a cervical collar. According to the methods of the invention, the cap is removed from the victim at the hospital, after which any residual scalp bleeding is treated with conventional means.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
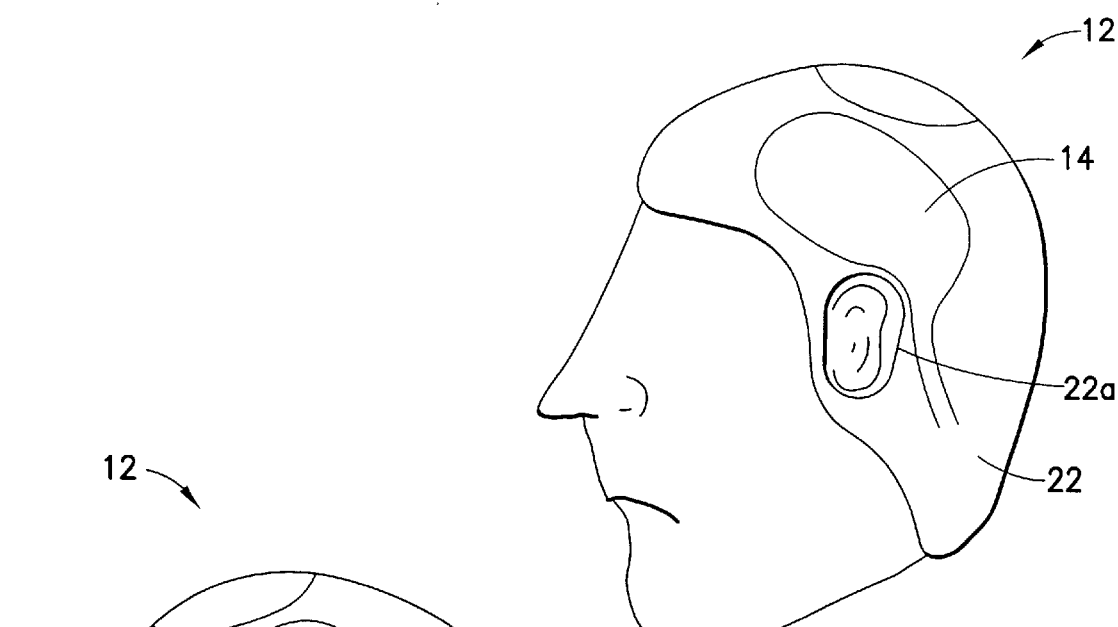
FIG. 1 is a partially transparent side elevation view of the left side of a first embodiment of an apparatus according to the invention.
Figure 2:
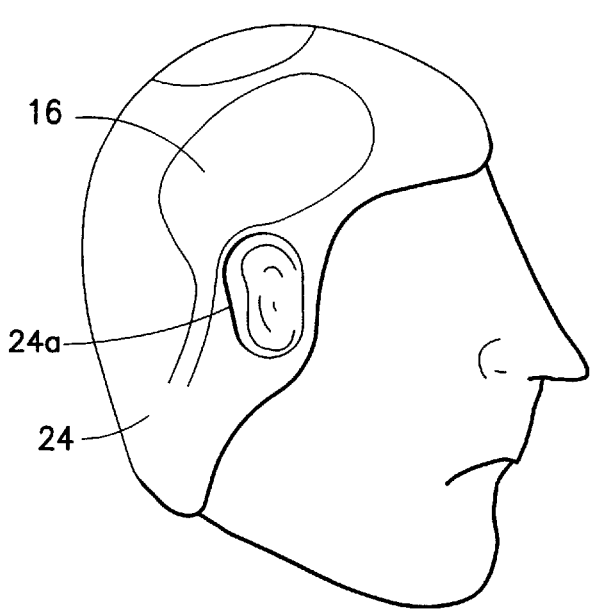
FIG. 2 is a partially transparent side elevation view of the right side of a first embodiment of an apparatus according to the invention.
Figure 3:
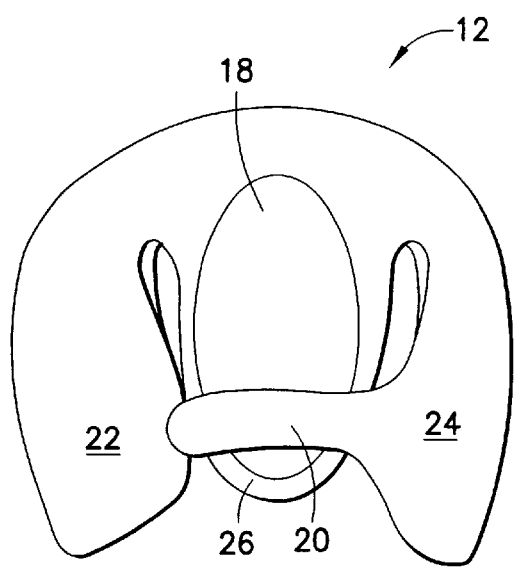
FIG. 3 is a partially transparent side elevation view of the back side of a first embodiment of an apparatus according to the invention.

Referring now to FIGS. 1 through 3, a first embodiment of an apparatus of the present invention includes a skull cap 12 having a plurality of inflatable bladders 14, 16, 18, and a VELCRO strap 20 for fastening it about the skull of a scalp wound victim. The configuration of the skull cap 12 includes three "lobes" 22, 24, 26 in which the inflatable bladders 14, 16, 18 are respectively located, which allow the cap to lie substantially flat when not fastened about a skull. The lobe 22 defines a left ear opening 22a and the lobe 24 defined a right ear opening 24a. According to the presently preferred embodiments, the cap is made from two layers: an inner rubber layer and an outer nylon/non-absorbent fabric layer. The bladders are preferably fluidly coupled to inflation tubes (not shown in FIGS. 1–3) having releasable valves which are located at a single location on the cap for rapid inflation with the pump. By arrangeing the cap as three lobes, it can lie flat when not in use and is easy to fit about different sized heads.

The skull cap 12 is fastened about the victim's skull with the left lobe 22 including bladder 14 overlying the left side of the skull with the victim's ear protruding through the ear opening 22a, and with the right lobe 24 including bladder 18 overlying the right side of the skull with the victim's ear protruding through the ear opening 24a. The back lobe 26 is arranged over the back of the skull between the other two lobes and the lobes are fastened to each other with the VELCRO strap as shown in FIG. 3 extending from one side of the victim's head across the back to the other side. After the cap 12 is fastened about the victim's skull, the bladders are inflated. According to the presently preferred embodiment, the bladders are inflated to a pressure of approximately 80 mm Hg using the hand pump described and illustrated below with reference to FIG. 5.

Figure 4:
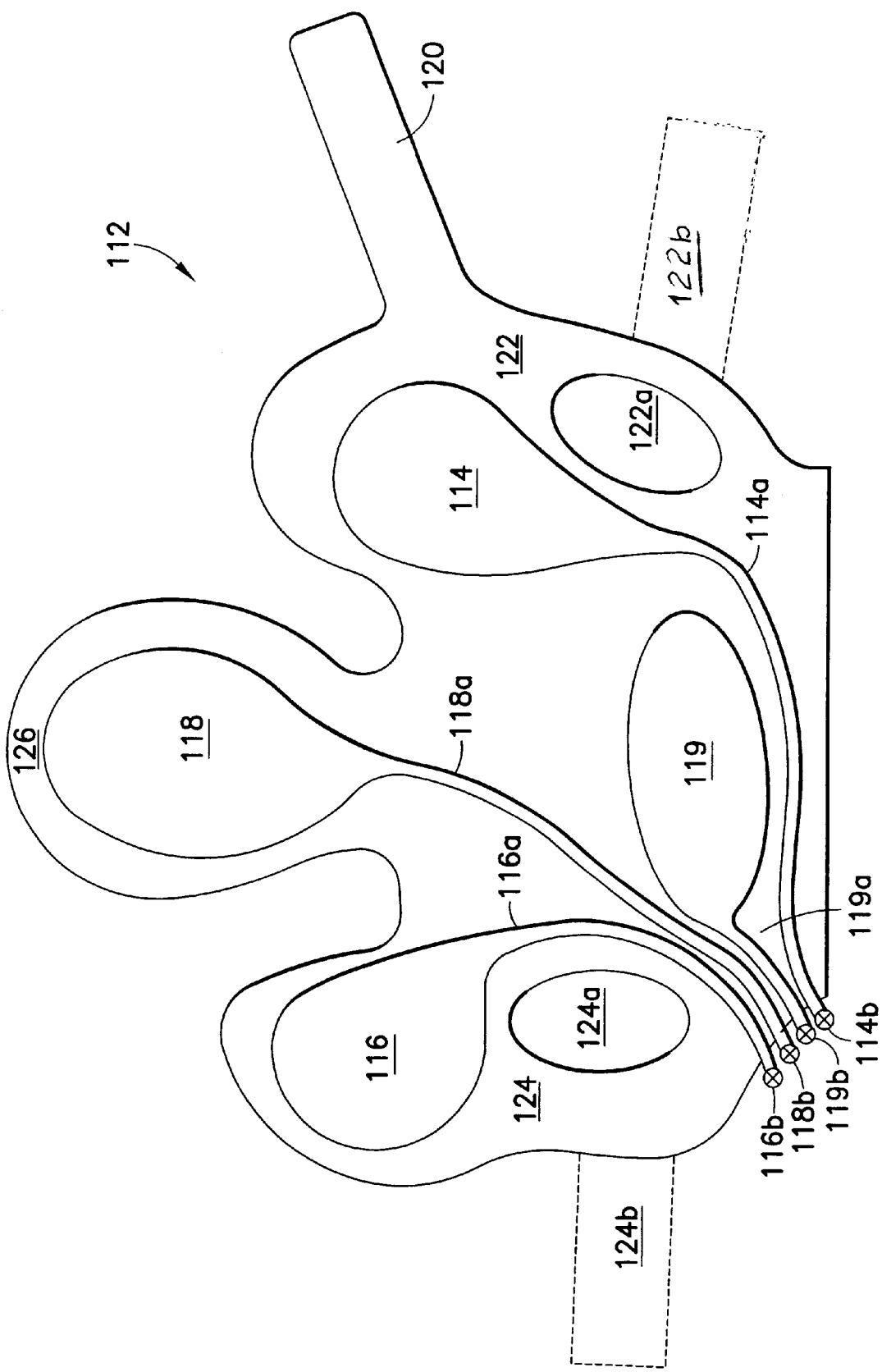
FIG. 4 is a partially transparent plan view of a second and presently preferred embodiment of the invention.

Referring now to FIG. 4, a second embodiment of a skull cap 112 is similar to the skull cap 12 with similar features being identified with similar numerals incremented by 100. According to this embodiment, the skull cap 112 has four bladders 114, 116, 118, 119 and a VELCRO fastening strap 120. The bladder 114 is located in a left side lobe 122 which defines an ear opening 122a. The bladder 116 is located in a right side lobe 124 which defines an ear opening 124a. The bladder 118 is located in a back of head lobe 126. According to this embodiment, the fourth bladder 119 is located in an area of the cap 112 between the side lobes 122 and 124 such that it will overlie the forehead when the cap is placed over the skull.

As mentioned above, the bladders are preferably each coupled to a fluid tube which terminates with a releasable valve at a single location. This is true for both embodiments and is illustrated in FIG. 4. As seen in FIG. 4, bladder 114 is coupled to tube 114a which terminates with releasable valve 114b; bladder 116 is coupled to tube 116a which terminates with releasable valve 116b; bladder 118 is coupled to tube 118a which terminates with releasable valve 118b; bladder 119 is coupled to tube 119a which terminates with releasable valve 119b. The releasable valves are preferably flapper valves with female luer slips, although other arrangements can be utilized. In addition, the valves 114b, 116b, 118b, and 119b are preferably located adjacent to each other for ease of use.

FIG. 4 also illustrates optional straps 122b, 124b depending from the side lobes 122, 124 respectively. These straps are designed to attach to a cervical collar. Cervical collars are frequently used in the case of traumatic head injury where there is the chance of central nervous system injury. Although two straps 122b, 124b are illustrated, more may be provided to enhance stability.

Figure 5:
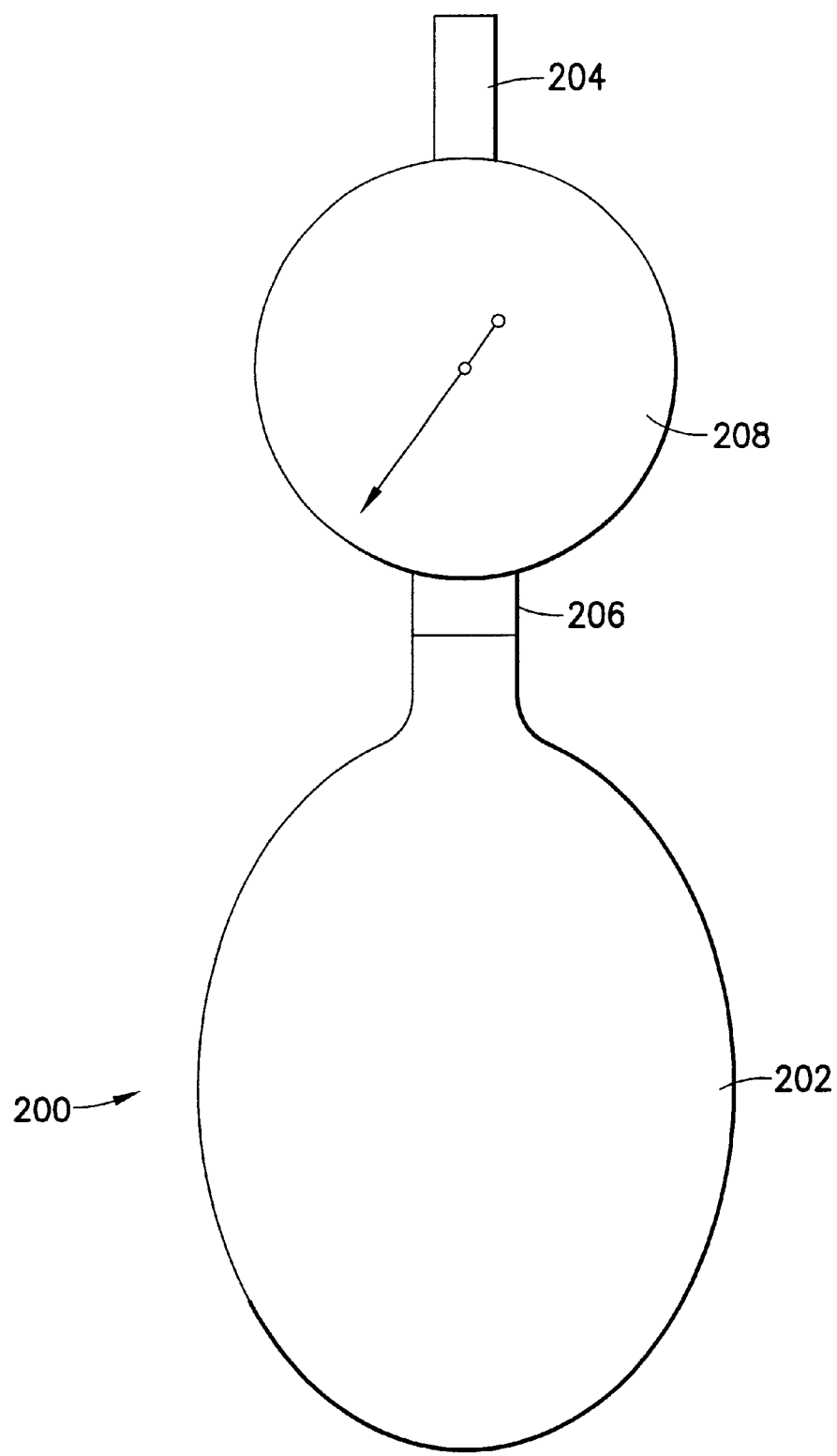
FIG. 5 is a side elevation view of a pump for use with the skull cap of the invention.

As mentioned above, the methods of the invention include fitting the cap to the skull of the victim and inflating the bladders with air. Any source of compressed air may be used to inflate the bladders, e.g. a compressed air tank, an electric pump, a foot operated pump, or a hand operated pump. According to the presently preferred embodiment, a hand operated pump is used because it is small, reliable, and easy to use. FIG. 5 illustrates the presently preferred type of pump 200 which is substantially similar to the type of pump used to inflate a blood pressure cuff. The pump 200 generally includes a squeezable bulb 202 having a one-way air inlet valve (not shown), an output nozzle 204 and a valve 206. Squeezing the bulb 202 causes air in the bulb to be forced through the valve 206 and out of the nozzle 204. The valve 206 prevents air from reentering the bulb 202 via the nozzle 204 when the bulb is released, but allows air to refill the bulb from the inlet valve (not shown). Also as mentioned above, the methods of the invention provide that the bladders be inflated to a pressure of approximately 80 mm Hg. In order to assist the emergency technician in performing this method, a pressure gauge 208 is also provided on the pump 200.

The presently preferred embodiment allows for bladders to be inflated individually so that a medical technician can choose to inflate fewer than all of the bladders if fewer than all are needed to effect hemostasis. Alternatively, all of the bladders can be coupled to a single valve so that all are quickly inflated together.

There have been described and illustrated herein several embodiments of methods and apparatus for arresting scalp bleeding. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other materials could be utilized. Also, while a hand pump has been shown, it will be recognized that other types of pumps could be used with similar results obtained. Moreover, while particular configurations have been disclosed in reference to a VELCRO fastener, it will be appreciated that other configurations could be used as well. Furthermore, while the skull cap has been disclosed as having three or four bladders, it will be understood that more bladders could be used but that if they are independently inflatable, it might take too long to inflate all of the bladders needed to effect the desired hemostasis. Thus, if many bladders are to be used, they should be fluidly linked in groups so that the bladders needed to effect the desired hemostasis can be inflated quickly. It will therefore be appreciated by those skilled in the art that yet other modifications could be made to the provided invention without deviating from its spirit and scope as so claimed.

What is claimed is:

1. An method for arresting scalp bleeding from a skull having a left side, right side, back and forehead, said method comprising:

a) fastening a skull cap having a plurality of inflatable bladders about the skull of a bleeding victim;

b) inflating the bladders such that pressure is exerted on the scalp sufficient to result in a hemostasis.

2. A method according to claim 1, wherein:

said step of inflating includes inflating at least three bladders.

3. A method according to claim 1, wherein:

said step of inflating includes inflating a first bladder which overlies the left side of the skull and a second bladder which overlies the right side of the skull.

4. A method according to claim 3, wherein:

said step of inflating includes inflating a third bladder which overlies the back of the skull.

5. A method according to claim 4, wherein:

said step of inflating includes inflating a fourth bladder which overlies the forehead.

6. A method according to claim 1, wherein:

said step of inflating is accomplished with a hand pump.

7. A method according to claim 1, wherein:

said step of inflating includes inflating a plurality of bladders to a pressure of approximately 80 mm Hg.

8. A method according to claim 1, further comprising:

c) coupling the skull cap to a cervical collar.

* * * * *